US006515749B2

(12) United States Patent
Pipino

(10) Patent No.: US 6,515,749 B2
(45) Date of Patent: Feb. 4, 2003

(54) SENSITIVE AND SELECTIVE CHEMICAL SENSOR WITH NANOSTRUCTURED SURFACES

(75) Inventor: Andrew C. R. Pipino, Gaithersburg, MD (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 0 days.

(21) Appl. No.: 09/924,576

(22) Filed: Aug. 9, 2001

(65) Prior Publication Data

US 2002/0122179 A1 Sep. 5, 2002

Related U.S. Application Data

(60) Provisional application No. 60/260,501, filed on Jan. 9, 2001.

(51) Int. Cl.[7] .......................... G01N 21/00; G07H 21/02
(52) U.S. Cl. .................. 356/440; 536/23.1; 536/22.1; 536/24.3; 359/296; 435/325; 422/82.05; 422/82.07
(58) Field of Search .................... 356/440, 441, 356/442, 432, 445, 736, 244, 317, 318; 250/227.21, 401.1; 435/325, 4–9; 422/82.05, 82.07, 82.09; 536/22.1, 23.1, 24.3, 6, 7.1; 359/296

(56) References Cited

U.S. PATENT DOCUMENTS 5,496,997 A * 3/1996 Pope ...................... 250/227.21
5,503,723 A * 4/1996 Ruddy et al. .............. 204/450
5,611,998 A * 3/1997 Aussengg et al. ....... 422/82.05
5,708,957 A * 1/1998 Chuang et al. .......... 422/82.07
5,835,231 A   11/1998 Pipino
5,943,136 A    8/1999 Pipino et al.
5,986,768 A   11/1999 Pipino
6,143,558 A * 11/2000 Kopelman et al. ....... 422/82.05
6,180,415 B1 * 1/2001 Schultz et al. ............. 356/317
6,219,137 B1 * 4/2001 Vo-Dinh ..................... 356/301
6,361,944 B1 * 3/2002 Mirkin et al. .................. 435/6

FOREIGN PATENT DOCUMENTS

DE       1 039 291     *  9/2000

* cited by examiner

Primary Examiner—Frank G. Font
Assistant Examiner—Sang H. Nguyen
(74) Attorney, Agent, or Firm—Larson & Taylor, PLC

(57) ABSTRACT

A chemical sensor is provided which includes an optical resonator including a nanostructured surface comprising a plurality of nanoparticles bound to one or more surfaces of the resonator. The nanoparticles provide optical absorption and the sensor further comprises a detector for detecting the optical absorption of the nanoparticles or their environment. In particular, a selective chemical interaction is provided which modifies the optical absorption of the nanoparticles or their environment, and an analyte is detected based on the modified optical absorption. A light pulse is generated which enters the resonator to interrogate the modified optical absorption and the exiting light pulse is detected by the detector.

20 Claims, 2 Drawing Sheets

SENSITIVE AND SELECTIVE CHEMICAL SENSOR WITH NANOSTRUCTURED SURFACES

RELATIONSHIP TO OTHER APPLICATIONS

This application claims benefit of the filing date of copending Provisional Patent Application No. 60/260,501, filed on Jan. 9, 2001, the disclosure of which is herein incorporated by reference.

FIELD OF THE INVENTION

The present invention relates, in general, chemical sensing and, more particularly, to an improved chemical sensor providing both selectivity and high sensitivity.

BACKGROUND OF THE INVENTION

Chemical sensing is fundamental to economic development, national security, and the quality of life. The demand for better sensing or detection technologies is ever-increasing to address needs in many different areas, such as the detection of concealed explosives in airports, chemical warfare agents that are fatal at extreme trace levels, or chlorine produced by chemical plants. To be effective, a chemical sensing technology must provide sufficient sensitivity and selectivity. Stability, robustness, and portability are also necessary or at least highly desirable characteristics. Therefore, any significant advance in current chemical sensing technology that improves sensitivity, selectivity, or adaptability will have a significant impact on national and global needs.

Although many transduction mechanisms exist for chemical sensing, optical absorption, in particular, is widely used. The ultimate sensitivity of an optical absorption measurement is limited by quantum noise arising from the discrete nature of light, although this limit is rarely achieved in practice. Recently, with the development of cavity ring-down spectroscopy (CRDS), the potential for routine quantum noise limited optical absorption measurements has become apparent. (See R. D. van Zee, J. T. Hodges, and J. P. Looney, *App. Opt.* 38, 3951 (1999)).

The principles and applications of CRDS are discussed, e.g., in (See A. O'Keefe and D. A. G. Deacon, *Rev. Sci. Instrum.* 59, 2544 (1988); *Cavity-Ringdown Spectroscopy*, K. W. Busch and M. A. Busch, eds. Coxford University Press, 1999) and these references, among others, may be consulted for a more complete discussion of CRDS. However, in brief, a typical gas-phase CRDS experiment, a stable optical cavity is formed from a pair of concave, highly reflective mirrors. When light, usually from a pulsed laser source, is injected into the cavity, the intensity of the circulating light decays exponentially with a frequency-dependent "ring-down" time, $\tau(\omega)$, given by the ratio of the round-trip time, $t_r$, to the sum of the round-trip losses, or $$\tau(\omega) = \frac{t_r}{L_0(\omega) + L_{abs}(\omega)}$$

where $L_0(\omega)$ is the intrinsic cavity loss and $L_{abs}(\omega)$ arises from absorption by gases contained within the cavity. The difference in intensity decay rates for gas-filled and empty cavities, as a function of laser frequency, provides the absolute absorption spectrum of the sample. Since the intensity decay rate ($\alpha 1/\tau$) is employed instead of a ratio of intensities, as in conventional absorption spectroscopy, the measurement is essentially immune to noise introduced by light source intensity fluctuations. The minimum detectable absorption in CRDS can be expressed as the product of the relative uncertainty in the ring-down time and the intrinsic cavity loss, or $(L_{abs})_{min}=L_0^*(\Delta T/T)=L_0^*\sqrt{2}\sigma_T/(T\sqrt{N})$ where $\sigma_T$ is the standard deviation of the ring-down time and N is the number of decay times averaged. (See P. Zalicki and R. N. Zare, *J. Chem. Phys.* 102, 2708, (1995); D. Romanini and K. K. Lehmann, *J. Chem. Phys.* 99, 6287–6301, (1993).) This expression for $(L_{abs})_{min}$ reveals both the simplicity and challenge of CRDS: minimize the intrinsic cavity loss and determine the ring-down time with the highest possible precision.

A variant of CRDS, termed evanescent wave cavity ring-down spectroscopy (EW-CRDS), has recently been developed, which permits application of CRDS to surfaces, films, and liquids. (See A. C. R. Pipino, J. W. Hudgens, R. E. Huie, *Rev. Sci. Instrum.* 68 (8), 2978, (1997); A. C. R. Pipino, J. W. Hudgens, R. E. Huie, *Chem. Phys. Lett.* 280, 104 (1997); A. C. R. Pipino in Proceedings of SPIE, Vol. 3535, Boston, Mass. (1998); A. C. R. Pipino, *Phys. Rev. Lett.* 83 (15), 3093–3096, (1999); A. C. R. Pipino in Proceedings of SPIE, 3858, Boston, Mass., (1999); A. C. R. Pipino, *Appl. Opt.* 39 (9), 1449 (2000); U.S. Pat. Nos. 5,835,231; 5,835,231; 5,986,768.) This technology is described in some detail in these references but in brief, EW-CRDS employs intra-cavity total internal reflection (TIR) to generate an evanescent wave at a resonator surface that allows optical absorption of condensed matter to be probed in a manner similar to attenuated total reflection (ATR) spectroscopy (see N. J. Harrick, Internal Reflection Spectroscopy, (Interscience Publishers, New York, (1967)), but with much higher sensitivity. In particular, a minuscule fraction ($<10^{-4}$) of a molecular layer of molecules can be detected at the TIR surface with EW-CRDS. Several resonator designs have been demonstrated for EW-CRDS, including variations that permit a miniature, robust optical absorption sensor to be achieved, thereby facilitating portability.

In many chemical sensing applications, detection of the analyte at a surface by direct absorption has major advantages. However, the analyte must have a significant absorption cross-section (or molar absorptivity) at the probe wavelength, which limits the minimum analyte concentration that can be detected. Typically, absorption cross-sections are largest for electronic transitions occurring in the visible region of the spectrum. Operation in the visible region also benefits from the availability of inexpensive sources including diode lasers, low-noise high-quantum efficiency detectors, and high transmission optical materials. However, many chemical species of interest do not have a significant visible absorption, and show instead significant absorption in the ultraviolet or infrared spectral regions. As discussed below, one aspect of the invention concerns circumventing this limitation.

One chemical sensing strategy that employs visible absorption, but permits detection of analytes that do not absorb at the probe wavelength, involves the use of surface plasmon polariton resonance (SPPR). This technology is described, for example, in J. Homola, S. S. Yee and G. Gauglitz, *Sens. Act. B*, 54, 3, (1999). In brief, SPPR is a surface electromagnetic wave that arises from the collective excitation of free electrons. A typical, conventional apparatus for making a SPPR measurement is shown at 10 in FIG. 1. In apparatus 10, a metal film 11 is deposited on the base of a prism 12, forming a three layer system consisting of the prism 12, the metal film 11, and the ambient medium indicated at 13. A visible laser beam, or a light beam from another visible light source, is denoted 14 and is incident on the metal film 11 at an angle of incidence $\theta_i$ that exceeds the critical angle, defined by $\theta_c = \sin^{-1}(n_o/n_i)$ where $n_i$ and $n_o$ are the refractive indexes of the material of the prism 12 and the ambient medium 13, respectively. Since $\theta_i > \theta_c$, total internal reflection occurs, giving rise to an evanescent wave 15. (See also N. J. Harrick, Internal Reflection Spectroscopy, (Interscience Publishers, New York, (1967).) For a certain angle $\theta_r$, with $\theta_i = \theta_r > \theta_c$, the evanescent wave 15 generated at the prism-metal interface excites the SPPR at the metal/ambient medium interface. The SPPR efficiently absorbs the incident light, trapping the electromagnetic energy in the form of a surface wave with a locally enhanced electric field.

The SPPR apparatus 10 is highly sensitive to environmental conditions at the metal/ambient medium interface. Hence, the angle of resonance, $\theta_r$, or the absorbance magnitude at a given $\theta_i$ near $\theta_r$, are very sensitive to chemical and physical interactions at the interface. In some cases, a reaction of the analyte occurs directly with the metal of the metal film 11. In other cases a thin film is applied to the metal that responds selectively to the analyte, changing in the local environment sensed by the SPPR apparatus 10. Both of these types of interactions can be highly selective for the specific analyte of interest. Sensors based on SPPR have been successful in both research and commercial applications. However, significant improvements in sensitivity are needed.

SUMMARY OF THE INVENTION

In accordance with the invention, a chemical sensor is provided which comprises an optical resonator with a nanostructured surface or surfaces that permit highly sensitive and selective chemical detection by absorption spectroscopy, advantageously in the visible spectral region. An important advantage of the invention is that the analyte is not required to have significant absorption cross section at the probe wavelength because, in contrast to conventional spectroscopy, detection is of the absorption of one or more of the nanoparticles bound to the resonator surface and forming the nanostructured surface. The nanoparticles have an enormous absorption cross section which is highly sensitive to the dielectric properties of the particle or the environment thereof and this enables the highly sensitive chemical detection mentioned above.

Generally speaking, the present invention relates to a chemical sensor comprising an optical resonator including a nanostructured surface comprising a plurality of nanoparticles bound to at least one surface of the resonator.

Preferably, the nanoparticles provide optical absorption and the sensor further comprises means for detecting the optical absorption of at least one of said nanoparticles.

In a preferred implementation, a selective chemical interaction is provided which modifies the optical absorption of one of (i) the at least one nanoparticle and (ii) the environment of the at least one nanoparticle, and an analyte is detected based on the modified optical absorption.

Advantageously, the sensor further comprises means for generating a light pulse which enters the resonator to interrogate the modified optical absorption, the detecting means comprising a detector for detecting the light pulse when the light pulse exits the resonator.

In one preferred embodiment, the selective chemical interaction mentioned above is provided by a direct chemical interaction between the at least one nanoparticle and the analyte which alters the absorption of the at least one nanoparticle.

In an alternative preferred embodiment, the at least one nanoparticle comprises a coated nanoparticle having a coating that selectively binds to the analyte to produce an effective coating refractive index change and the aforementioned selective chemical reaction comprises the selective binding of the coating to the analyte.

Advantageously, the at least one nanoparticle comprises a plurality of nanoparticles which support a surface plasmon polariton resonance.

In an advantageous implementation, the at least one nanoparticle comprises a nanoparticle selected from the group consisting of gold, silver, cadmium sulfide and zinc selenide nanoparticles.

In a further advantageous implementation, the at least one nanoparticle comprises a nanoparticle selected from the group consisting of spherical, spheroidal, and tetrahedral nanoparticles. In a particularly beneficial embodiment for some applications, the at least one nanoparticle comprises a gold nanosphere.

In one preferred embodiment, the at least one surface comprises an ultra-smooth polished surface and the optical resonator comprises a resonator employing intracavity total internal reflection so as to permit the use of evanescent wave cavity ring-down spectroscopy in probing the modified optical absorption.

In one important application, the sensor is used to detect $NO_2$ and nitrocompounds and the nanoparticles comprise gold nanoparticles.

In a further important application, the sensor is used to detect volatile organic compounds and said nanoparticles have a coating of cyclodextrin molecules.

In accordance with a further aspect of the invention, a chemical sensor is provided which comprises a resonator providing intracavity total internal reflection and comprising first and second opposed planar coated facets and a further convex facet acting as a total internal reflection surface; a light source for producing a light pulse which enters through said first coated surface and exits through said second coated surface; a plurality of nanoparticles covalently attached to said convex surface so as to absorb an evanescent field produced by said convex surface.

Preferably, the nanoparticles comprise gold nanospheres. Advantageously, the light pulse comprises a laser pulse.

According to a further aspect of the invention, there is provided a chemical sensor comprising a resonator defining a cavity, a light source for generating light which enters said cavity, the resonator providing intracavity total internal reflection of said light, and including at least one surface having a plurality of nanoparticles bound thereto such that the optical absorption of at least one of the nanoparticles, or of the environment of the nanoparticles, is modified in response to a selective chemical interaction, the sensor further comprising means for detecting an analyte based on the modified optical absorption.

As above, in one implementation, the selective chemical interaction is provided by a direct chemical interaction between the at least one nanoparticle and the analyte which alters the absorption of the at least one nanoparticle.

Also as above, in an alternative implementation, the at least one nanoparticle comprises a coated nanoparticle having a coating that selectively binds to the analyte to produce an effective coating refractive index change and said selective chemical reaction comprises the selective binding of the coating to the analyte.

Again, the at least one nanoparticle preferably comprises a nanoparticle selected from the group consisting of gold, silver, cadmium sulfide and zinc selenide nanoparticles, and in some important applications, comprises a plurality of gold nanospheres.

Further features and advantages of the present invention will be set forth in, or apparent from, the detailed description of preferred embodiments thereof which follows.

BRIEF DESCRIPTION OF THE DRAWINGS

FIG. 3 is a schematic diagram, partially in block form, of a chemical sensor (resonator) constructed in accordance with one embodiment of the invention, while

DESCRIPTION OF THE PREFERRED EMBODIMENTS

Figure 1:
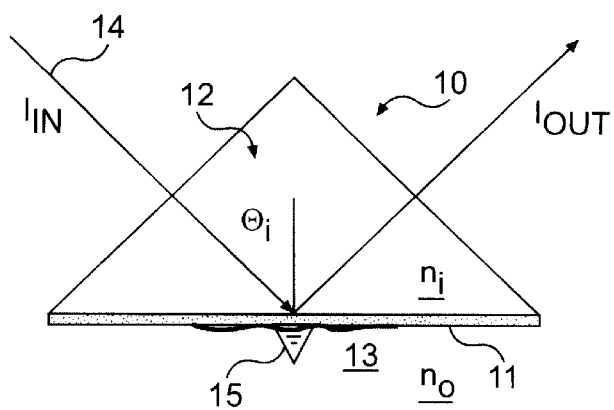
FIG. 1, which was discussed above, is a schematic diagram of conventional (prior art) apparatus for making a SPPR measurement.

As indicated above, in accordance with the invention, a chemical sensing system is provided in which the sensing surface of an optical resonator is modified to: 1) increase the number of chemical species that can be detected by absorption, 2) increase selectivity, and 3) optimize sensitivity. As indicated previously, many chemical species do not have a significant visible absorption and that this is a problem in that a number of advantages accrue from operating in the visible region of the spectrum. In accordance with one aspect of the invention, a chemically modified optical surface is provided which possesses a visible absorption that responds to a wide range of analytes without requiring a significant absorption cross-section at the probe wavelength. Since the TIR surfaces used for EW-CRDS and all intra-cavity surfaces of CRDS resonators have a typical root-mean-square surface roughness of 0.05 nm chemical modification and functionalization (see N. J. Brown, *Annu. Rev. Mater. Sci.* 16, 371, (1986)), these surfaces provide a unique and advantageous template for uniform attachment rate at a surface (see K. C. Grabar, P. C. Smith, M D. Musick, J. A. Davis, D. G. Walter, M. A. Jackson, A. P. Guthrie and M. J. Natan, *J. Am. Chem. Soc.*, 118, 1148, (1996)).

The invention increases the number of chemical species that can be detected by shifting the probe wavelength for all chemical species to a single, convenient wavelength, which is typically in the visible region, where optimal light sources, detectors, and optical materials already exist.

The analyte is not required to have a significant absorption cross-section at the probe wavelength. Increased selectivity is achieved by chemically modifying the sensing surface to maximize chemical interactions with the analyte through control of, for example, hydrophobic, hydrophilic, or stearic effects, while minimizing interactions with interfering agents. Finally, chemical detection sensitivity can be optimized since the choice of probe wavelength is flexible, being dependent on nanoparticle shape, size, and material. This flexibility allows wavelength-dependent factors such as light source power, detector quantum efficiency, and optical material transmission to be optimally chosen.

Although this invention is intended to extend and enhance the capabilities of EW-CRDS, the invention is equally applicable to other optical transduction chemical detection technologies, where sensing at a surface occurs.

As set forth above, one aspect of the present invention concerns the provision of a nanostructured surface, i.e., an assembly of nanoparticles, in a low loss optical resonator. In a preferred embodiment, this approach is combined with SPPR. The optical absorption of metal nanoparticles results in a strong visible absorption that arises from SPPR excitation. These surface modes depend strongly on the shape of the particle and the dielectric properties of the metal. Both thin films and small particles are examples of systems with at least one small dimension (see C. F. Bohren and D. R. Huffman, *Absorption and Scattering of Light by Small Particles*, chap. 8, Wiley & Sons, New York, (1983)). Hence, the same sensitivity to surface chemical phenomena that is observed with SPPR excitation at a metal thin film can be anticipated for metal nanoparticles. Indeed, large changes in the absorbance of nanoparticles have been observed with selective chemical binding at the surface of nanoparticles in a bulk solution. (See Liu, S. Mendoza, E. Roman, M. J. Lynn, R. Xu, and A. E. Kaifer, *J. Am. Chem. Soc.* 121, 4304, (1999).) Nanoparticles have also been deposited on or attached to surfaces. Visible absorption measurements have been used to characterize the shape of particles on a surface (see R. Jensen, G. C. Schatz, and R. P. Van Duyne, *J. Phys. Chem. B*, 103, 2394, (1999)) or to monitor the chemical attachment rate at a surface (see K. C. Grabar, P. C. Smith, M D. Musick, J. A. Davis, D. G. Walter, M. A. Jackson, A. P. Guthrie and M. J. Natan, *J. Am. Chem. Soc.*, 118, 1148, (1996)).

In general, the invention, in one aspect, may be thought of as comprising three basic "components": 1) a low loss optical resonator, 2) an assembly of nanoparticles, and 3) a selective chemical interaction or selective coating. These components will be considered separately below.

Many different resonator designs or constructions may be employed as the low loss optical resonator. Some specific useful resonator designs are described in U.S. Pat. Nos. 5,835,231, 5,943,136, and 5,986,768, all of which were mentioned above.

One class of resonators, which is described in U.S. Pat. No. 5,943,136, employs multiple optical elements including intra-cavity prisms possessing at least one TIR surface and high reflectivity mirrors. The resonators of this class are large in size (~0.1–1 meter) and the useful spectral range is typically limited by the bandwidth of the high reflectivity mirror coatings. Since multiple optical elements are employed, including prisms, this class of resonators also typically possesses multiple intra-cavity surfaces where reflection losses can occur. These reflection losses can be minimized by the use of anti-reflection coatings or by orienting the surface(s) at Brewster's angle, which minimizes reflection losses for a single polarization direction.

A second class of resonators, which is described in U.S. Pat. No. 5,986,768, is based on a monolithic design in which high-reflectivity coated surfaces and TIR surfaces are both integral to a single element. This design, which can be miniaturized, eliminates the intra-cavity surfaces that incur reflection losses. An arbitrarily polarized optical beam can also be utilized, which permits polarization-dependent measurements. The bandwidth of the high-reflectivity optical coatings employed restricts the useful spectral range for this class of resonators.

A third class of resonators, which is described in U.S. Pat. No. 5,835,231, employs a polygonal TIR-ring design that utilizes photon tunneling for light input and output. The TIR-ring resonator has a broad spectral bandwidth, supports arbitrary polarization, and is inherently miniature. Designs can also be employed that use optical flats or wedges inside a linear resonator.

All of the three resonator classes for EW-CRDS described above employ intra-cavity TIR at ultra-smooth surfaces. These surfaces are homogenized by the polishing process used, thereby providing highly uniform and isotropic starting surfaces for chemical functionalization.

Figure 2A:
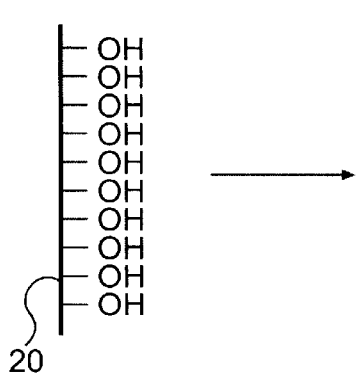
FIGS. 2(a)–2(d) are schematic representations of the steps involved in a method of constructing a chemical selective surface with molecular recognition sites.
Figure 2B:
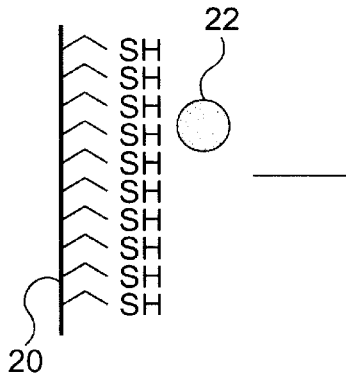
Figure 2D:
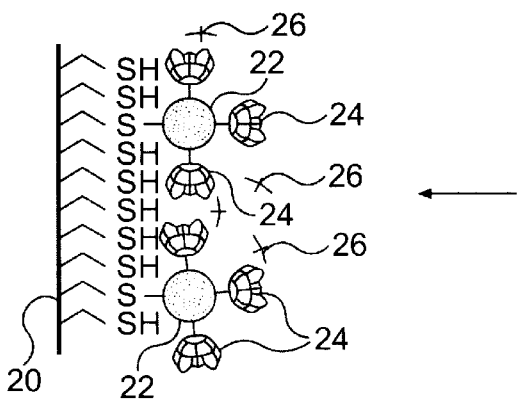
Figure 2C:
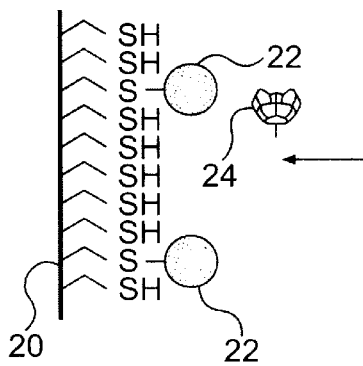

Referring to FIGS. 2(a) to 2(d), there is shown an exemplary construction of a chemically selective surface with molecular recognition (MR) sites on gold nanoparticles, indicated at 22. In this example, a fused-silica or sapphire resonator has ultra-smooth TIR surfaces, indicated by fused silica surface 20, terminated with surface hydroxl (—OH) groups, as shown in FIG. 2(a). The nanoparticles 22 can be attached to the resonator surface 20 through reaction with the surface hydroxyls. For example, a highly ordered alkanethiol self-assembled monolayer (SAM) can be formed which can act as a linker layer for attachment of the gold nanoparticles 22 through a covalent bond to the terminal thiol group and the gold surface. In the example shown in FIG. 2(b), a monolayer of, e.g., (ω-mercaptoalkylsilane, is first formed on the ultra-smooth fused-silica surface 20, and the terminal —SH groups anchor the gold nanoparticles 22. As shown in FIG. 2(c). the gold nanoparticles 22 are, in turn, functionalized with a chemically selective MR site. In the example shown, the nanospheres 22 are functionalized with molecular "cavitands" 24 which selectively interact with percholoreythylene (PCE) molecules 26, as discussed below.

As indicated in the example just described, the nanoparticles used can be nanospheres, which are readily available in a range of sizes. Gold nanospheres have absorption cross sections in the range of $1 \times 10^{-15}$ to $1 \times 10^{-11}$ cm$^2$/particle for the 1–30 nm particle size range (see C. F. Bohren and D. R. Huffman, *Absorption and Scattering of Light by Small Particles*, chap. 8, Wiley & Sons, New York, (1983)). The peak absorption wavelength occurs at 520 nm, which is approximately independent of sphere diameter.

The optical absorption properties of the nanospheres 22 can be rigorously modeled by employing Lorenz-Mie theory, which also describes to a good approximation the absorption of nanospheres bound to a weakly interacting dielectric surface, such as the surface of an EW-CRDS resonator.

It will be understood that other particle shapes or materials can also be utilized which allow the peak absorption wavelength to be shifted from its size-independent value for spherical particles. For example, truncated tetrahedral silver particles have been formed which have a peak absorption wavelength of 620 nm and a peak absorption cross section of $10^{-11}$ cm$^2$/particle (see T. R. Jensen, G. C. Schatz, and R. P. Van Duyne, *J. Phys. Chem. B*, 103, 2394, (1999)). These tetrahedral particles are formed by vapor deposition of silver using a simple polystyrene nanosphere mask, which permits control of particle size, aspect ratio, and surface density.

Figure 3:
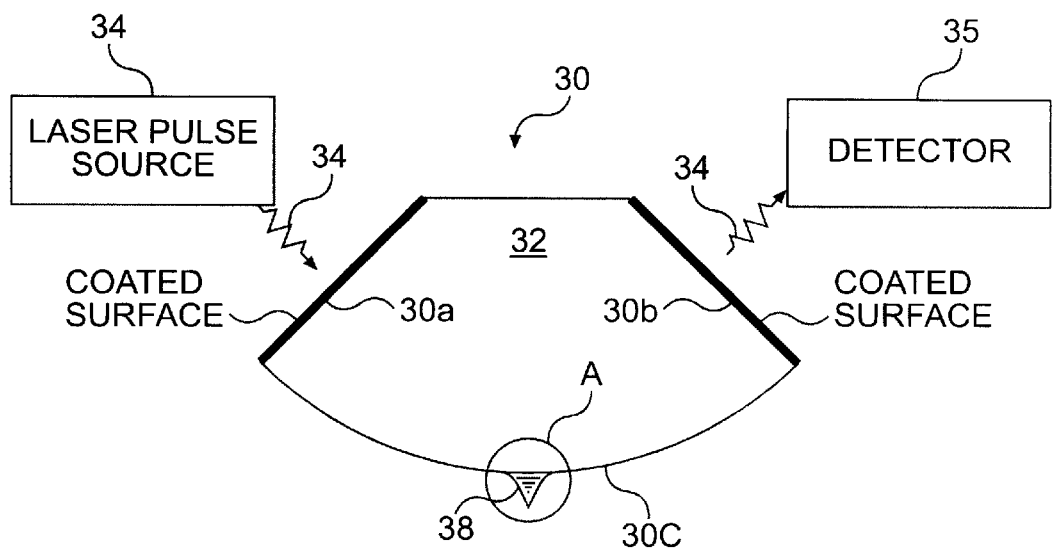
Figure 3A:
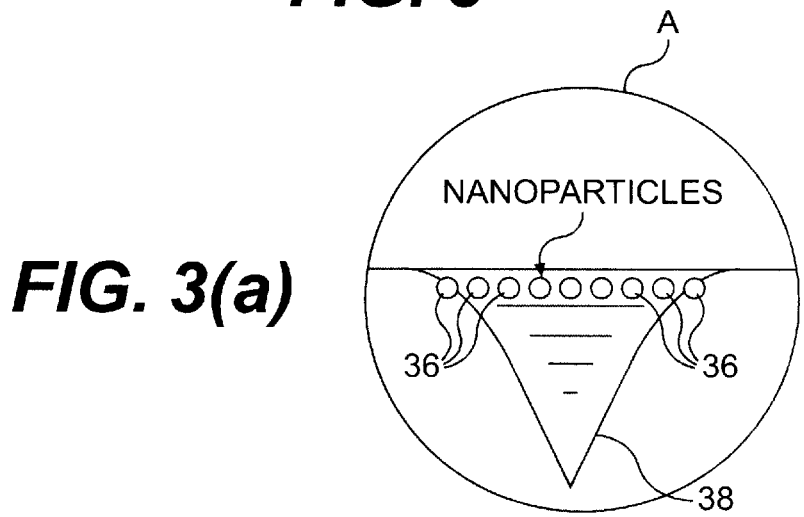
FIG. 3(a) is a detail of region A of FIG. 3 drawn to an enlarged scale.

In general, the size, shape, and surface density of nanoparticle assemblies at the surface of an EW-CRDS resonator can be controlled, thus permitting the total optical loss and peak absorption wavelength to be selected. The sensitivity of the EW-CRDS measurement can thereby be optimized. A specific embodiment incorporating a monolithic, folded resonator as described in U.S. Pat. No. 5,986,768, is depicted in FIG. 3, and in FIG. 3(a) which shows a detail of region A of FIG. 3. The resonator, which is generally denoted 30, defines a cavity 32 and includes two opposed coated planar surfaces or facets 30a and 30b and a convex surface or facet 30c. Light, which is indicated at 34 and can comprise a laser pulse from a laser pulse source 33, enters and exits the resonator 30 through the opposite planar, coated facets 30a and 30b, respectively, while the convex facet 30c is a TIR surface. The exiting light 34 is received by a detector 35. As shown in FIG. 3(a), nanoparticles 36, e.g., gold nanospheres, are covalently attached to the convex TIR surface 30c where the nanospheres 36 absorb the concomitant evanescent field or wave 38 produced at that surface. In other words, a nanostructured surface is formed by covalently bonding an assembly of nanospheres 36 to facet 30c. The optical properties of the nanospheres 36 are probed with a high sensitivity by the evanescent wave 38, the latter being generated by TIR at the convex surface 30c as just described. Selectivity is achieved by functionalizing the nanoparticles 36 to respond to a specific analyte. Specific examples of selective chemical interactions occurring at the nanostructured surface are described below.

An example of a direct selective chemical interaction with nanoparticles is demonstrated by detection of $NO_2$ and nitrocompounds with uncoated gold nanospheres. It will be appreciated that quantitative detection of $NO_2$ is important for characterizing internal combustion engines, propulsion, factory emissions, and the like. Many explosives are also nitro-based, such as trinitrotoluene and nitroglycerine. Therefore, a sensitive and selective detection system for nitrocompounds would find wide application.

Figure 4:
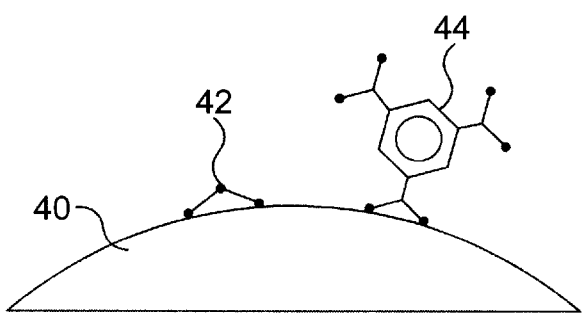
FIG. 4 is a schematic representation of the bonding of $NO_2$ and TNT to a gold nanosphere.

In the embodiment under consideration, selective and sensitive detection of $NO_2$ with gold nanospheres is achieved because gold, which is typically inert with respect to most chemical agents, interacts strongly but reversibly with $NO_2$ to form a bidentate bond between the two oxygen atoms and the gold surface. This is shown schematically in FIG. 4 wherein a gold nanosphere is indicated at 40 and the $NO_2$ and TNT are indicated at 42 and 44, respectively. Surface spectroscopic studies of $NO_2$ on single crystals of gold (see J. Wang and B. E. Koel, *J. Phys. Chem. A* 102, 8573, (1998)) and polycrystalline foils (see D. T. Wickham, B. A. Banse, and B. E. Koel, *Catalysis* 6, 163, (1990)) have confirmed this interaction.

It is noted that detection of $NO_2$ with conventional SPPR techniques using a thin gold film deposited on a prism hypotenuse has demonstrated a 0.1% change in signal intensity for a 1 part-per-million change in the vapor phase concentration of $NO_2$ (see G. J. Ashwell and M. P. S. Roberts, *Electr. Lett.* 32 (22), 2089, (1996)). Selectivity was demonstrated by detecting $NO_2$ in the presence of $NH_3$, $H_2$, CO, $CO_2$, $SO_2$, HCl, $Cl_2$, and $H_2S$, at concentrations of 100 ppm.

A chemical sensor as shown in FIG. 3 provides a new approach to fully exploiting this unique interaction, where gold nanospheres are employed. In contrast to conventional SPPR, where measurement precision is typically limited to 0.1% with integration times on the order of 1 second, a minimum detectable signal change of 0.03% is possible with CRDS using only a single laser pulse with an effective integration time of a few microseconds. Furthermore, gold nanospheres have a high density of steps at the sphere surface that show a particular tendency to bind $NO_2$, as revealed by the studies on polycrystalline foils to which reference was made above. Therefore, a much lower detection limit can be achieved for a given signal integration time by employing the present invention. In addition, the new technology described above can be miniaturized, which increases commercial viability.

As mentioned above, another type of selective chemical interaction that occurs at the surface of a nanoparticle involves the use of selective coatings. For example, detection of volatile organic compounds (VOCs) can be accomplished using cyclodextrin molecules as chemical receptor "buckets" tailored to accommodate a specific class of molecules (see J. Liu, S. Mendoza, E. Roman, M. J. Lynn, R. Xu, and A. E. Kaifer, *J. Am. Chem. Soc.* 121, 4304, (1999)). Cyclodextrins possess hydrophobic cavities which bind an organic guest molecule reversibly through Van der Waals and hydrogen bonding interactions. These guest-host inclusion complexes can be optimized for a particular class of molecules. Cyclodextrins can also be bound to gold nanoparticles.

As illustrated schematically in FIGS. 2(a) to 2(d) and in particular in FIG. 2(d), molecular buckets termed "cavitands," which are derived from resorcin[4]arenes, can be bound to gold nanoparticles, and these particular cavitands have also shown high selectivity (see Schierbaum, K. D.; Weiss, T.; van Velzen, E. U. T.; Engbersen, J. F. J; Reinhoudt, D. N.; Gopel, W. *Science* (1994), 265, 1413). When molecules bind to cyclodextrin, resorcin[n]arene, or similar molecular cavities attached to nanoparticles, an effective change in the thickness or refractive index of the coating is induced. This change in coating properties correspondingly induces a change in the nanoparticle absorption cross-section, which can be sensitively detected using the present invention.

In comparison to the inventions described in U.S. Pat. Nos. 5,835,231, 5,943,136, 5,986,768, the present invention provides for detection of analytes that do not show appreciable optical absorption at the wavelength of operation. Thus, the present invention provides a significant advance in generality. In comparison to conventional SPPR techniques, the present invention utilizes the sensitivity of SPPR while providing higher measurement precision of analyte-induced changes in the SPPR signal through the use of CRDS detection. These improvements in precision, which provide higher sensitivity, are achieved with a comparatively simple measurement system, which can also be miniaturized. Finally, the present invention also provides higher sensitivity and greater simplicity than existing optical absorption techniques that are not based on the use of CRDS. It will be understood that a sensing technology based on CRDS provides immunity to light source fluctuations and allows near shot-noise-limited detection (see R. D. van Zee, J. T. Hodges, and J. P. Looney, *Appl. Opt.* 38, 3951 (1999)).

As indicated above, a chemical sensor in accordance with the present invention is useful in many different areas including the detection of the following: explosives, chlorinated hydrocarbons such as perchloroethylene (PCE) or trichloroethylene (TCE), $NO_x$, volatile organic compounds (VOC's), halogens, heavy metals, chemical warfare agents, and other chemical species.

Although the invention has been described above in relation to preferred embodiments thereof, it will be understood by those skilled in the art that variations and modifications can be effected in these preferred embodiments without departing from the scope and spirit of the invention.

What is claimed:

1. A chemical sensor comprising an optical resonator including a nanostructured surface comprising a plurality of nanoparticles bound to at least one surface of the resonator.

2. A sensor as claimed in claim 1 wherein said nanoparticles provide optical absorption and said sensor further comprises means for detecting the optical absorption of at least one of said nanoparticles.

3. A sensor as claimed in claim 1 wherein a selective chemical interaction is provided which modifies the optical absorption of one of (i) at least one nanoparticle and (ii) the environment of the at least one nanoparticle, and an analyte is detected based on the modified optical absorption.

4. A sensor as claimed in claim 3 wherein said sensor further comprises means for generating a light pulse which enters the resonator to interrogate the modified optical absorption, said detecting means comprising a detector for detecting the light pulse when the light pulse exits the resonator.

5. A sensor as claimed in claim 3 wherein said selective chemical interaction is provided by a direct chemical interaction between the at least one nanoparticle and the analyte which alters the absorption of the at least one nanoparticle.

6. A sensor as claimed in claim 3 wherein said at least one nanoparticle comprises a coated nanoparticle having a coating that selectively binds to the analyte to produce an effective coating refractive index change and said selective chemical reaction comprises the selective binding of the coating to the analyte.

7. A sensor as claimed in claim 3 wherein said at least one nanoparticle comprises a plurality of nanoparticles which support a surface plasmon polariton resonance.

8. A sensor as claimed in claim 3 wherein said at least one nanoparticle comprises a nanoparticle selected from the group consisting of gold, silver, cadmium sulfide and zinc selenide nanoparticles.

9. A sensor as claimed in claim 3 wherein said at least one nanoparticle comprises a nanoparticle selected from the group consisting of spherical, spheroidal, and tetrahedral nanoparticles.

10. A sensor as claimed in claim 3 wherein said at least one nanoparticle comprises a gold nanosphere.

11. A sensor as claimed in claim 3 wherein said at least one surface comprises an ultra-smooth polished surface and said optical resonator comprises a resonator employing intracavity total internal reflection so as to permit the use of evanescent wave cavity ring-down spectroscopy in probing the modified optical absorption.

12. A sensor as claimed in claim 1 wherein said sensor is used to detect $NO_2$ and nitrocompounds and said nanoparticles comprise gold nanoparticles.

13. A sensor as claimed in claim 1 wherein said sensor is used to detect volatile organic compounds and said nanoparticles have a coating of cyclodextrin molecules.

14. A chemical sensor comprising a resonator providing intracavity total internal reflection and comprising first and second opposed planar coated facets and a further convex facet acting as a total internal reflection surface; a light source for producing a light pulse which enters through said first coated surface and exits through said second coated surface; a plurality of nanoparticles covalently attached to said convex surface so as to absorb an evanescent field produced by said convex surface.

15. A sensor as claimed in claim 14 wherein said nanoparticles comprise gold nanospheres.

16. A sensor as claimed in claim 14 wherein said light pulse comprises a laser pulse.

17. A chemical sensor comprising a resonator defining a cavity, a light source for generating light which enters said cavity, said resonator providing intracavity total internal reflection of said light, and including at least one surface having a plurality of nanoparticles bound thereto such that the optical absorption of one of (i) at least one of the nanoparticles and (ii) the environment of the nanoparticles is modified in response to a selective chemical interaction, said sensor further comprising means for detecting an analyte based on the modified optical absorption.

18. A sensor as claimed in claim 17 wherein said selective chemical interaction is provided by a direct chemical interaction between the at least one nanoparticle and the analyte which alters the absorption of the at least one nanoparticle.

19. A sensor as claimed in claim 17 wherein said at least one nanoparticle comprises a coated nanoparticle having a coating that selectively binds to the analyte to produce an effective coating refractive index change and said selective chemical reaction comprises the selective binding of the coating to the analyte.

20. A sensor as claimed in claim 17 wherein said at least one nanoparticle comprises a nanoparticle selected from the group consisting of gold, silver, cadmium sulfide and zinc selenide nanoparticles.

* * * * *